(12) United States Patent
Okuyama et al.

(10) Patent No.: US 8,679,145 B2
(45) Date of Patent: Mar. 25, 2014

(54) PUNCTURE DEVICE

(75) Inventors: Koji Okuyama, Ehime (JP); Akio Nagao, Kagawa (JP); Yoshiki Takeuchi, Ehime (JP)

(73) Assignee: Panasonic Corporation, Osaka (JP)

( * ) Notice: Subject to any disclaimer, the term of this patent is extended or adjusted under 35 U.S.C. 154(b) by 658 days.

(21) Appl. No.: 12/921,224

(22) PCT Filed: Mar. 6, 2009

(86) PCT No.: PCT/JP2009/001028
§ 371 (c)(1),
(2), (4) Date: Sep. 7, 2010

(87) PCT Pub. No.: WO2009/110247
PCT Pub. Date: Sep. 11, 2009

(65) Prior Publication Data
US 2011/0015662 A1    Jan. 20, 2011

(30) Foreign Application Priority Data
Mar. 7, 2008  (JP) .................................. 2008-058436

(51) Int. Cl.
A61B 17/34 (2006.01)
(52) U.S. Cl.
USPC ........................................................ 606/181
(58) Field of Classification Search
USPC ........................................ 606/181, 182, 583
See application file for complete search history.

(56) References Cited

U.S. PATENT DOCUMENTS

| | | | | |
|---|---|---|---|---|
| 5,554,166 A | * | 9/1996 | Lange et al. | 606/182 |
| 2004/0243165 A1 | * | 12/2004 | Koike et al. | 606/181 |
| 2005/0288698 A1 | * | 12/2005 | Matsumoto | 606/181 |
| 2009/0163944 A1 | * | 6/2009 | Nagao et al. | 606/181 |

FOREIGN PATENT DOCUMENTS

| | | |
|---|---|---|
| JP | 7-16218 | 1/1995 |
| JP | 2005-312763 | 11/2005 |
| WO | 03/005907 | 1/2003 |
| WO | 2004/010871 | 2/2004 |
| WO | 2007/129757 | 11/2007 |

* cited by examiner

Primary Examiner — Thomas McEvoy
Assistant Examiner — Julie A Szpira
(74) Attorney, Agent, or Firm — Wenderoth, Lind & Ponack, L.L.P.

(57) ABSTRACT

A puncture device capable of preventing needle stick accidents and of reducing the burden on patients during operation. In this puncture device, a puncture needle cartridge comprises: a lancet body having a puncture needle at one end with the other end being to be held by a puncture instrument body; a protective cap; and a puncture needle holder engaged with the lancet body to rotate together with the lancet body about a rotation axis P. A mounting member rotates together with the puncture needle holder with a boss guided by a slit through being pressed by the puncture needle cartridge in a direction of mounting in a case, and is mounted in the case. The protective cap, formed integrally with the lancet body, is prevented from rotating by being grasped and is separated from the lancet body with the rotation of the mounting member.

11 Claims, 17 Drawing Sheets

PUNCTURE DEVICE

TECHNICAL FIELD

The puncture device of the present invention relates to a puncture device for blood sampling in blood measurements including, in particular, blood sugar measurements.

BACKGROUND ART

Various puncture instruments for blood sampling and disposable lancets used therewith have conventionally been developed. Such a puncture instrument would have a risk that a user sticks a puncture needle, exposed from one end of a lancet, into the user's hand or the like by mistake when the user attaches or removes the lancet to or from the puncture instrument.

Responding to the above-mentioned problem and in order to eliminate the risk of a hand or the like directly touching a puncture needle, puncture needle cartridges have been developed which removably attach to a puncture instrument a lancet having a cap surrounding a puncture needle (e.g. see Patent related documents 1, 2, and 3).

These puncture needle cartridges comprise: a lancet body having a puncture needle at one end and a chuck portion to be chucked by the puncture instrument at the other end; and a protective cap provided separably from the lancet body, and a user uses a disposable puncture needle cartridge attaching and removing it to and from the puncture instrument. At the time of puncture, a user uses it after twisting and cutting off and separating the protective cap from the lancet body.

[Patent related document 1] Japanese Patent Laid-Open Application No. 2005-312763

[Patent related document 2] WO 2003/005907

[Patent related document 3] Japanese Patent Laid-Open Application No. Hei 7-16218

DISCLOSURE OF THE INVENTION

Problems to be Solved by the Invention

The above-mentioned conventional configuration, however, causes a state where if the protective cap is pulled out with the protective cap not twisted and cut off or not sufficiently twisted and cut off, normal engagement between the chuck portion of the lancet and a plunger of the puncture instrument for chucking the chuck portion breaks off, so that the depth of puncture changes, the needle tip of the lancet is exposed from the puncture instrument, or the like. As a result, the above-mentioned conventional configuration would have a problem of the risk of a needle stick accident caused by the exposed needle.

In order to solve the above problem, there is a possible mechanism by which the separation of the lancet body and the protective cap is ensured with the lancet body chucked properly by the puncture instrument and if the chuck of the lancet body comes off due to incorrect operation, the protective cap is prevented from being separated from the puncture needle cartridge so that a needle stick accident may be prevented.

This mechanism, however, also leaves a problem of inconvenience caused by the required operation to twist and cut off the protective cap, similarly to conventional puncture needle cartridges.

A purpose of the invention is to provide a puncture device capable of preventing needle stick accidents and of reducing the burden on patients during operation.

Means for Solving the Problems

A puncture device of the invention comprises: a puncture needle cartridge having: a rod-like lancet body having a puncture needle at one end with the other end being to be held by a puncture instrument body; a protective cap for protecting the puncture needle and formed integrally with the lancet body; and a puncture needle holder engaged with the lancet body to rotate together with the lancet body about a shaft center of the lancet body; a mounting member for holding the puncture needle cartridge such that the puncture needle cartridge can be inserted and removed; and a case mounted with the mounting member and held by the puncture instrument body, and has a mechanism by which: the case has a guiding portion for guiding the rotation of the mounting member about the axis of rotation; the mounting member is engaged with the puncture needle holder and rotates together with the puncture needle holder about the axis of rotation with a guided portion guided by the guiding portion through being pressed by the puncture needle cartridge in a direction of mounting in the case; and the protective cap is prevented from rotating about the axis of rotation during the press and is separated from the lancet body with the rotation of the mounting member about the axis of rotation.

A puncture device of the invention comprises: a puncture needle cartridge having: a rod-like lancet body having a puncture needle at one end with the other end being to be held by a puncture instrument body; a protective cap for protecting the puncture needle and formed integrally with the lancet body; and a puncture needle holder engaged with the lancet body to rotate together with the lancet body about a shaft center of the lancet body; a mounting member for holding the puncture needle cartridge such that the puncture needle cartridge can be inserted and removed; and a case mounted with the mounting member and held by the puncture instrument body, and has a mechanism by which: the mounting member is engaged with the puncture needle holder and rotates together with the puncture needle holder about the axis of rotation through a guiding portion guiding a guided portion formed on the case when pressed by the puncture needle cartridge in a direction of mounting in the case; and the protective cap is prevented from rotating about the axis of rotation during the press and is separated from the lancet body with the rotation of the mounting member about the axis of rotation.

Advantages of the Invention

This invention allows the operation of twisting and cutting off the protective cap to be carried out in parallel with the operation of inserting the puncture needle cartridge into the puncture instrument body, and can therefore prevent needle stick accidents and reduce the burden on patients during operation.

BEST MODE OF EMBODYING THE INVENTION

Now, embodiments of the invention will be described in detail with reference to the drawings.

Embodiment 1

Figure 1:
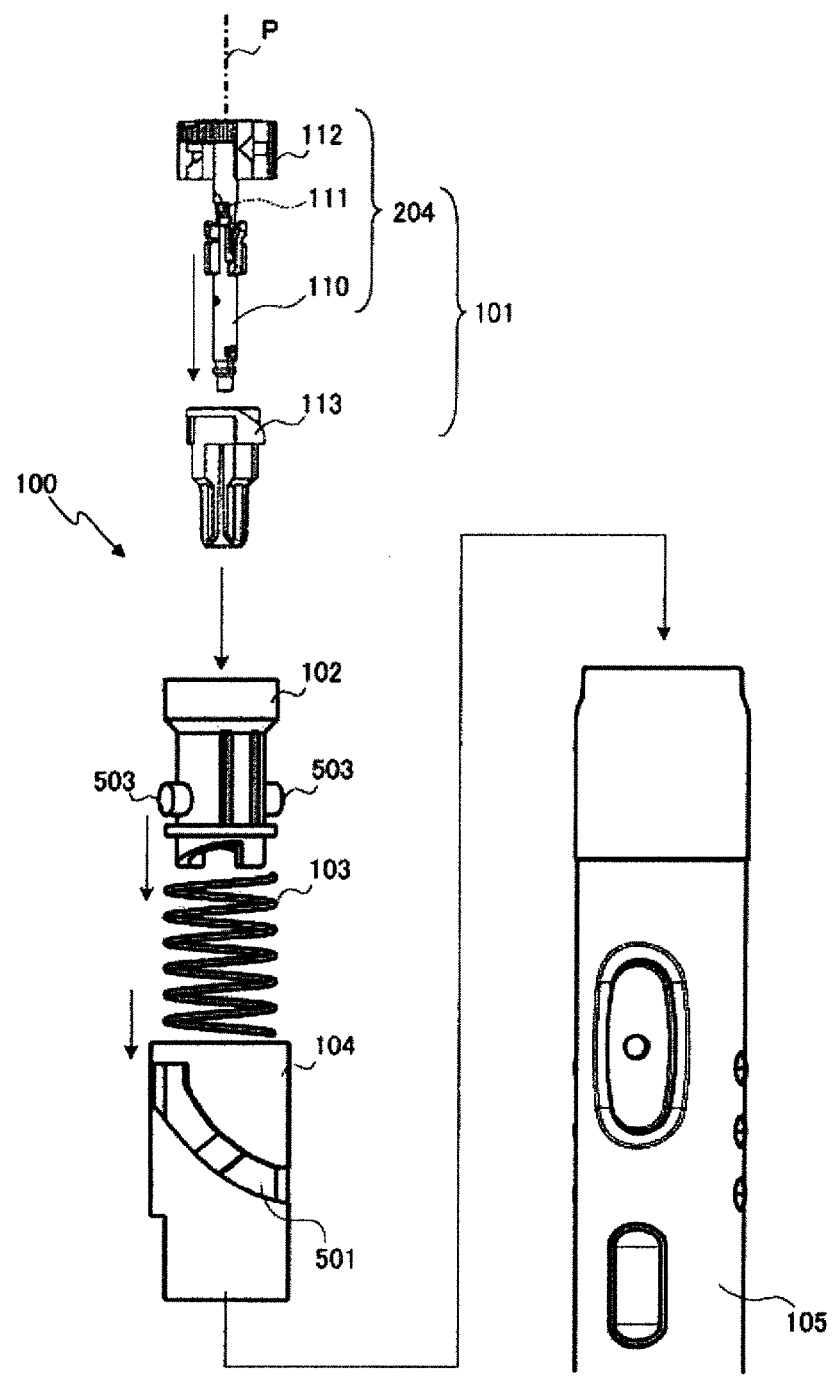
FIG. 1 is an exploded front view of a puncture device according to Embodiment 1 of the invention.

FIG. 1 is an exploded front view of a puncture device 100 according to Embodiment 1 of the invention.

The puncture device 100 mainly comprises a puncture needle cartridge 101, a mounting member 102, a return spring 103, a case 104, and a puncture instrument body 105. The mounting member 102, the return spring 103, and the case 104 are attached in advance to the puncture instrument body 105.

The puncture needle cartridge 101, inserted within the mounting member 102, is engaged with the mounting member 102, presses the mounting member 102 in a mounting direction of the mounting member 102 (the downward direction in FIG. 1), and is received within the front end (the upper end in FIG. 1) of the puncture instrument body 105.

The mounting member 102 holds the puncture needle cartridge 101 such that it can be inserted and removed and, received within the later-described case 104, is attached in advance together with the case 104 in the puncture instrument body 105. At that time, the mounting member 102 is attached in the puncture instrument body 105, cooperating with the case 104 to put the return spring 103 therebetween. A boss 503, which is a guided portion of the mounting member 102, is placed in a slit 501 of the case 104 and moves along the slit 501 with the movement of the mounting member 102 in the case 104 without being disengaged from the slit 501. The mounting member 102, when the puncture needle cartridge 101 is not inserted therein, is pressed in an ejection direction (the upward direction in FIG. 1) by a biasing force of the return spring 103 and partly sticks out of the front end of the puncture instrument body 105. The mounting member 102 is also engaged with a later-described puncture needle holder 113. The mounting member 102 then rotates together with the puncture needle holder 113 with the boss 503 guided by the slit 501 through being pressed by the puncture needle cartridge 101 in the direction of mounting in the case 104.

The return spring 103 is a coil spring formed of an elastic member, and is received in the case 104 with the lower end being in contact with the inside bottom surface of the case 104. When the boss 503 of the mounting member 102 is placed in the slit 501 of the case 104, the return spring 103 is pressed in the mounting direction by the mounting member 102 and, elastically deformed between the mounting member 102 and the inside bottom surface of the case 104, is received within the case 104.

The case 104 is tubular and internally holds the mounting member 102 and the return spring 103. The case 104 also has the slit 501 as a guiding portion for guiding the rotation of the mounting member 102 about a rotation axis P. The slit 501 is engaged with the boss 503 of the mounting member 102 to guide the rotation of the mounting member 102.

The puncture needle cartridge 101 mainly comprises a lancet body 110, a puncture needle 111, a protective cap 112, and the puncture needle holder 113.

Figure 4:
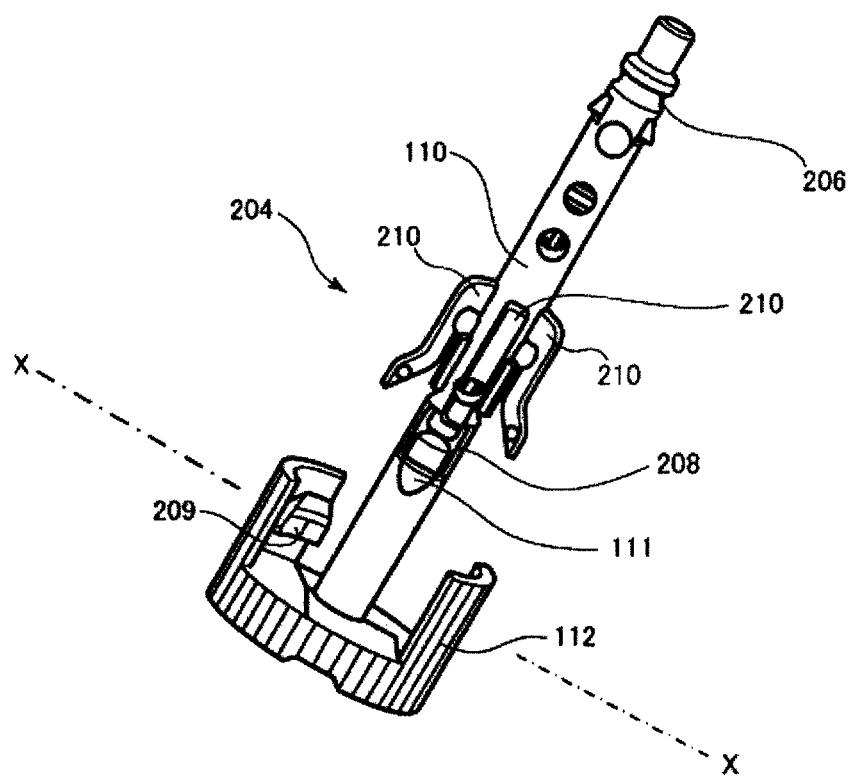
FIG. 4 is a perspective view of a lancet according to Embodiment 1 of the invention.

The lancet body 110 is rod-like, and has the puncture needle 111 near one end, and at the other end a chuck portion 206 (see FIG. 4) to be held by the puncture instrument body 105. The lancet body 110 is formed integrally with the protective cap 112 covering the puncture needle 111. A connection 208 shown in FIG. 4 is formed on the lancet body 110, so that the protective cap 112 is separated at the connection 208 when the mounting of the puncture needle cartridge 101 in the mounting member 102 is completed.

Since the protective cap 112 is separated and removed during blood sampling, the front end of the puncture needle 111 is exposed from the lancet body 110, and this allows the puncture needle 111 to puncture.

Even at this time, however, the front end of the puncture needle 111 is held inside below the front ends of the puncture instrument body 105 and mounting member 102, and therefore safety is assured. That is, as long as a user does not hold down a puncture button (not shown) of the puncture instrument 100, the front end of the puncture needle 111 does not stick out of the puncture instrument body 105.

The protective cap 112 covers the puncture needle 111 to protect it, and is formed integrally with the lancet body 110. The protective cap 112 is grasped by a user's hand when the user presses the mounting member 102 in the mounting direction through the puncture needle cartridge 101, and therefore the rotation of the protective cap 112 is prevented even when the lancet body 110 and the puncture needle holder 113 rotate together with the mounting member 102. For that purpose, the top surface (surface to be pushed by a hand or finger of a user) of the protective cap 112 has an uneven shape not to be slippery. The protective cap 112 is separated from the lancet body 110 when the mounting of the puncture needle cartridge 101 in the puncture instrument body 105 is completed.

The puncture needle holder 113 is engaged with the mounting member 102, and rotates together with the mounting member 102 about the shaft center of the lancet body 110, the rotation axis P, when the mounting member 102 is pressed in the mounting direction by the puncture needle cartridge 101. The puncture needle holder 113 is also engaged with the lancet body 110 and, when rotating together with the mounting member 102 about the shaft center of the lancet body 110, the rotation axis P, rotates the lancet body 110 together with itself. At this time, since the protective cap 112 is grasped by a hand of a user, the rotation about the shaft center of the lancet body 110, the rotation axis P, is prevented and the load on the connection between the protective cap 112 and the lancet body 110 breaks the connection, so that the protective cap 112 and the lancet body 110 are separated from each other. As a result, the puncture needle 111 is exposed from one end of the lancet body 110.

Figure 2:
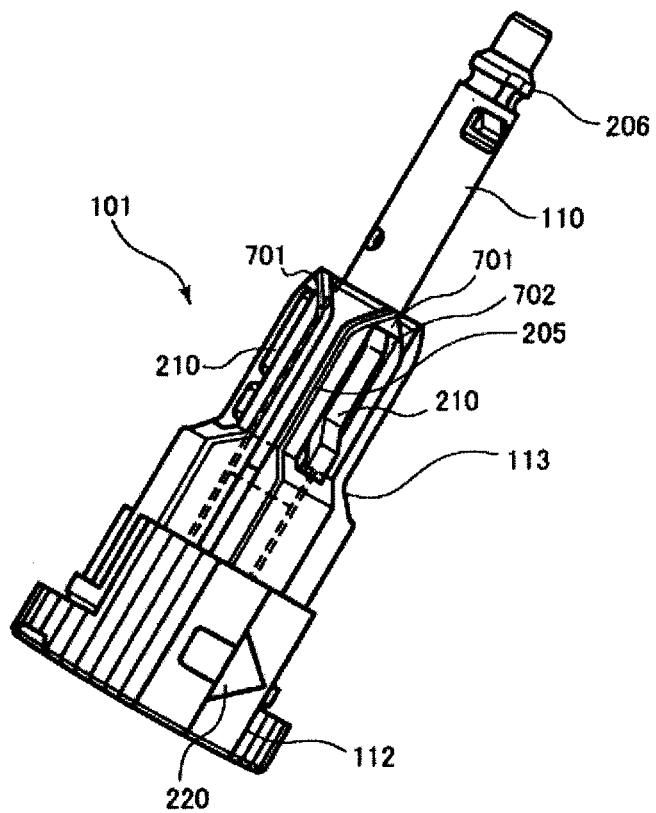
FIG. 2 is a front view of a puncture needle cartridge according to Embodiment 1 of the invention.
Figure 3:
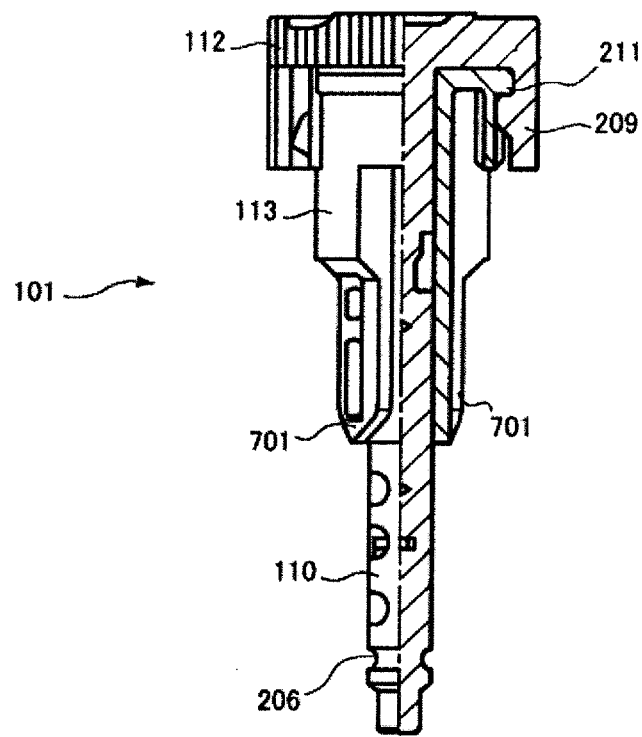
FIG. 3 is a partially sectional view of the puncture needle cartridge, which is partially cut away, according to Embodiment 1 of the invention.
Figure 5:
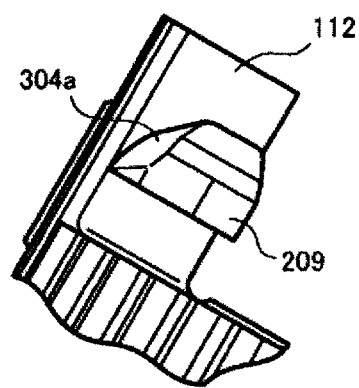
FIG. 5 is an enlarged view of part of a protective cap according to Embodiment 1 of the invention.
Figure 6:
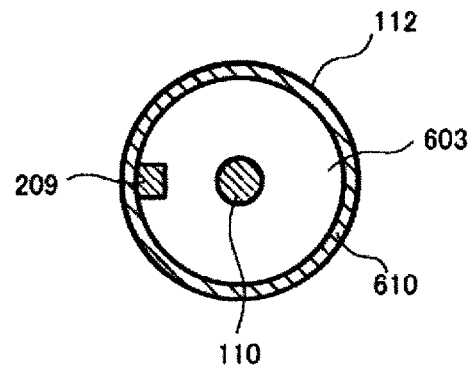
FIG. 6 is a cross sectional view cut along a line X-X of FIG. 4.
Figure 7:
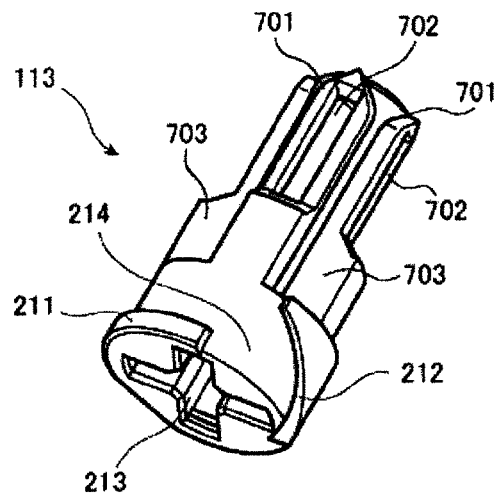
FIG. 7 is a perspective view of a puncture needle holder according to Embodiment 1 of the invention.
Figure 8:
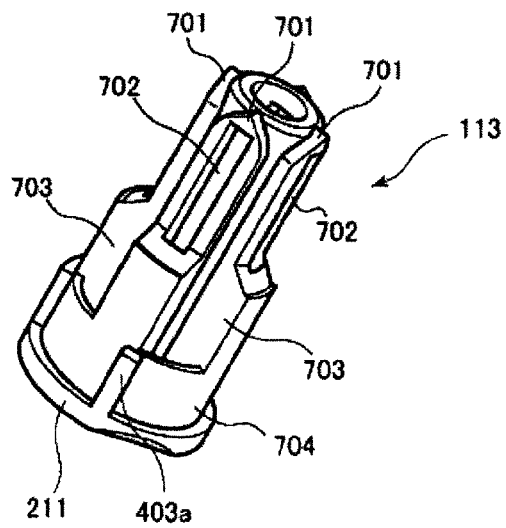
FIG. 8 is a perspective view of the puncture needle holder according to Embodiment 1 of the invention.
Figure 9:
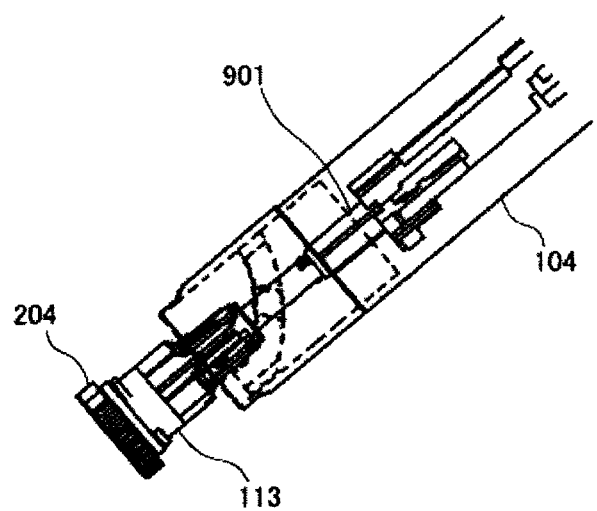
FIG. 9 is a front view of part of the puncture device according to Embodiment 1 of the invention.

The puncture needle cartridge 101 will next be described with reference to FIGS. 2 to 9. Now, FIG. 2 is a front view of the puncture needle cartridge 101. FIG. 3 is a partially sectional view of the puncture needle cartridge 101, which is partially cut away, in an initial position. FIG. 4 is a perspective view of a lancet 204 comprising the lancet body 110 and protective cap 112. FIG. 5 is an enlarged view of part of the protective cap 112. FIG. 6 is a cross sectional view cut along a line X-X of FIG. 4. FIGS. 7 and 8 are perspective views of the puncture needle holder 113. FIG. 9 is a transparent front view of the puncture needle cartridge 101 mounted in the puncture instrument body 105. FIGS. 7 and 8 are perspective views of the puncture needle holder 113 viewed from different directions.

The puncture needle cartridge 101 mainly comprises the puncture needle holder 113 and the lancet 204.

As shown in FIG. 4, the lancet 204 mainly comprises the lancet body 110 and the protective cap 112. As shown in FIG. 2, the lancet 204 is received in the inside 205 of the tubular puncture needle holder 113. As shown in FIG. 4, the lancet body 110 and the protective cap 112 are integrally formed of resin material (e.g. polyethylene resin) or the like, and are separably connected with each other at the connection 208.

As shown in FIG. 4, the lancet body 110 is rod-like, and has the puncture needle 111 near one end and a chuck portion 206 at the other end. As shown in FIG. 9, the puncture needle cartridge 101 comprising the puncture needle holder 113 and the lancet 204 is fixedly attached inside the front end of the puncture instrument body 105. At this time, the chuck portion 206 is grasped by a front end of a plunger 901 of the puncture instrument body 105.

As shown in FIG. 4, the protective cap 112 covers the puncture needle 111 held by the lancet body 110, thereby protecting the puncture needle 111. If the protective cap 112 rotates a predetermined angle about the shaft center of the lancet body 110, the rotation axis P, the connection between the protective cap 112 and the lancet body 110 breaks at the connection 208. That is, "separably" means that if the protective cap 112 is rotated a predetermined angle about the shaft center of the lancet body 110, the rotation axis P, the connection 208 breaks or the engagement therebetween is released, allowing them to be separated from each other. In order for the protective cap 112 to be broken at the connection 208 and be separated from the lancet body 110, an arrow 220 which is a mark indicating a rotation direction in which the protective cap 112 should be rotated is given on the protective cap 112 as shown in FIG. 2. As shown in FIG. 6, the protective cap 112 is tubular with a hollow 603, and is provided with a lug portion 209 which protrudes in the hollow 603 from a wall portion 610 formed around the hollow 603. As shown in FIG. 5, the lug portion 209 has a slope portion 304a. The slope portion 304a of the lug portion 209 comes in contact with a later-described slope portion 212 (see FIG. 7) when the protective cap 112 rotates a predetermined angle about the shaft center of the lancet body 110, the rotation axis P.

As shown in FIGS. 3, 7, and 8, the puncture needle holder 113 has a flange portion 211 formed parallel with the rotation direction of the puncture needle holder 113. When the puncture needle holder 113 is engaged with the lancet 204, the flange portion 211 is engaged with the lug portion 209 of the protective cap 112 as shown in FIG. 3. As shown in FIG. 7, the puncture needle holder 113 is provided with four tongue portions 701 having a free end elastically deformable in a direction perpendicular to the mounting direction of the mounting member 102. On each tongue portion 701 is formed a long hole 702 which is a through hole in which a cross-shaped rib 210 of the lancet 204 is engaged. Consequently, the engagement between the lug portion 209 and the flange portion 211 (see FIG. 3) and the engagement between the long holes 702 and the cross-shaped rib 210 (see FIG. 2) prevent a user or the like from pulling out the protective cap 112 from the puncture needle holder 113 in a direction opposite to the mounting direction of the mounting member 102 (the upward direction in FIG. 3). So, if a user pulls the protective cap 112 of the puncture needle cartridge 101 mounted in the puncture instrument body 105 with the intention of separating the protective cap 112 from the lancet body 110 without rotating the protective cap 112 about the rotation axis P, the user has to remove it together with the puncture needle cartridge 101 from the puncture instrument body 105. For this reason, even an action of a user trying to forcedly pull out the protective cap 112 does not cause: a release of the normal grasp of the lancet body 110 by the puncture instrument (the plunger); a change in the depth of puncture; or protrusion of the tip of the puncture needle 111 of the lancet 204 from the puncture instrument, and needle stick accidents caused by the protruding puncture needle 111 can also be prevented.

As shown in FIG. 7, the puncture needle holder 113 has the slope portion 212 which guides the protective cap 112 when the protective cap 112 rotates about the shaft center of the puncture needle holder 113, the rotation axis P. The puncture needle holder 113 is also provided with a cross-shaped groove 213 formed to project on a position corresponding to the position of each tongue portion 701 and made through in the direction of the rotation axis P as shown in FIG. 7. When engaged with the cross-shaped rib 210 (see FIG. 4) provided on the lancet 204, the cross-shaped groove 213 limits the rotation between the puncture needle holder 113 and the lancet 204 about the rotation axis P in an initial state. As shown in FIG. 3, the flange portion 211 is positioned to be engaged with the lug portion 209 of the protective cap 112 in the initial state. As shown in FIG. 7, the flange portion 211 is provided with a notch 214 so that the engagement with the lug portion 209 of the protective cap 112 (see FIGS. 5 and 6) is released when the protective cap 112 rotates a determined amount about the shaft center of the lancet body 110, the rotation axis P. On the puncture needle holder 113, as shown in FIG. 8, a limit portion 403a is formed to project outward on an insertion portion 704 to be inserted into the mounting member 102, the limit portion 403a being for limiting the rotation of the protective cap 112 in the opposite direction (the direction opposite to the rotation direction indicated by the arrow 220 in FIG. 2).

As shown in FIGS. 7 and 8, on the puncture needle holder 113 is formed four cuts 703 which are engaged with later-described projections 601 of the mounting member 102 (see FIG. 11) to limit the rotation of the puncture needle holder 113 against the mounting member 102 about the shaft center, the rotation axis P. The cuts 703 are each formed between the tongue portions 701 formed to project on the insertion portion 704.

Figure 10:
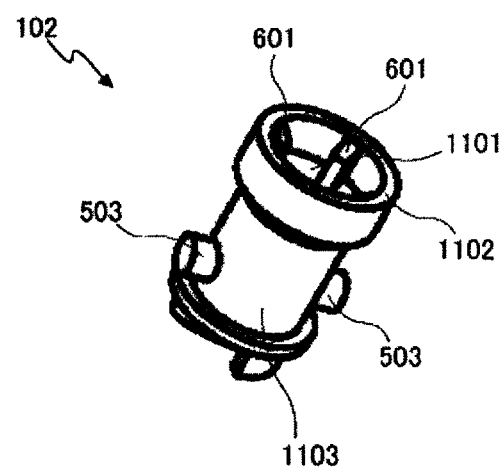
FIG. 10 is a perspective view of a mounting member according to Embodiment 1 of the invention.
Figure 11:
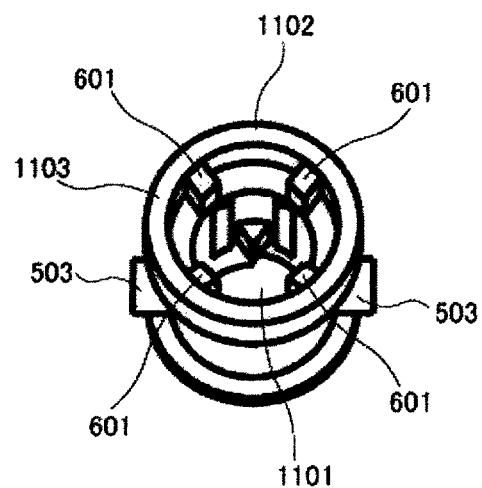
FIG. 11 is a perspective view of the mounting member according to Embodiment 1 of the invention.
Figure 12:
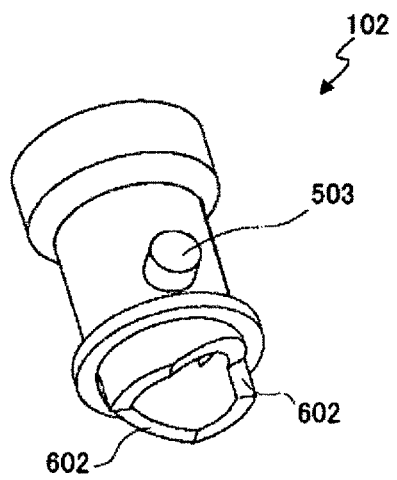
FIG. 12 is a perspective view of the mounting member according to Embodiment 1 of the invention.
Figure 13:
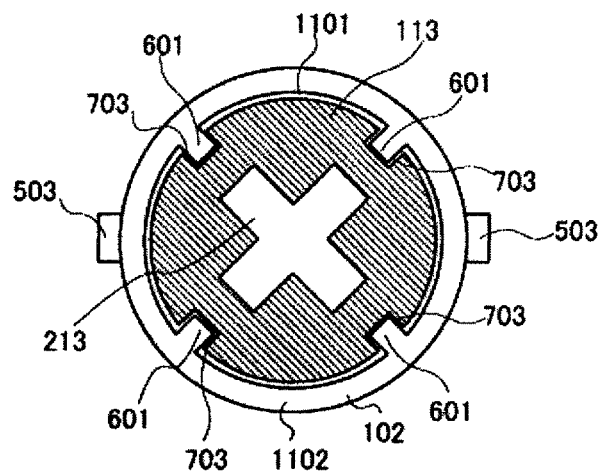
FIG. 13 is a sectional view of the mounting member with the puncture needle holder inserted therein according to Embodiment 1 of the invention.

The mounting member 102 will next be described with reference to FIGS. 10 to 13. Now, FIGS. 10 to 12 are perspective views of the mounting member 102, each of which is viewed from different directions. FIG. 13 is a cross sectional view showing the projections 601 of the mounting member 102 and the cuts 703 of the puncture needle holder 113 being engaged with one another.

The mounting member 102 is tubular with a hollow 1101 for inserting the puncture needle cartridge 101. The four projections 601 to be engaged with the cuts 703 of the puncture needle holder 113 comprising the puncture needle cartridge 101 are also formed on the mounting member 102 integrally therewith to project in the hollow 1101 from a wall portion 1102 formed around the hollow 1101. As shown in FIG. 13, the projections 601 are engaged with the cuts 703 of the puncture needle holder 113. Consequently, when the mounting member 102 rotates clockwise or counterclockwise within the case 104, that is, when the boss 503 of the mounting member 102 moves along the slit 501 of the case 104, the puncture needle holder 113 and the mounting member 102 work in an integrated manner. The mounting member 102 also has a slope portion 602 at the lower end as shown in FIG. 12. The slope portion 602 is configured to be able to be engaged with a later-described triangular lug 802 of an ejection rod 801 incorporated in the puncture instrument body 105 (see FIG. 18) to release the locked state with the case 104 when the lancet body 110 is disposed of after being used for the puncture. The mounting member 102 has two bosses 503 formed to project outward from a wall portion 1103 formed around the hollow 1101. The boss 503 is engaged with the slit 501 of the case 104 described later, movably along the slit 501. The numbers of the bosses 503 and slits 501 each are not limited to two. The numbers of the bosses 503 and slits 501 each may be one, or three or more.

Figure 14:
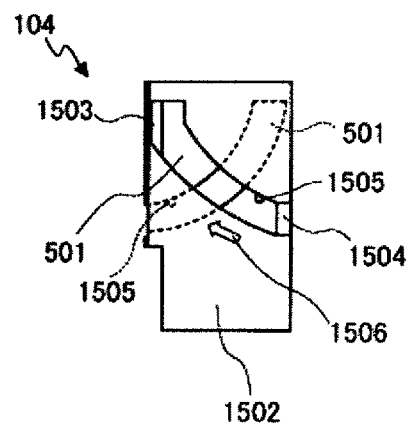
FIG. 14 is a front view of a case according to Embodiment 1 of the invention.
Figure 15:
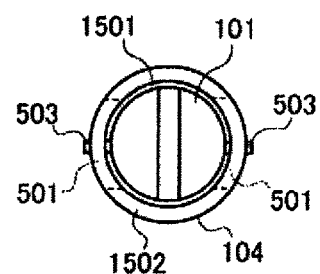
FIG. 15 is a top view of the case with the puncture needle cartridge inserted therein according to Embodiment 1 of the invention.

The case 104 will next be described with reference to FIGS. 14 and 15. FIG. 14 is a front view of the case 104. FIG. 15 is a top view of the case 104 with the puncture needle cartridge 101 inserted therein, viewed from the top.

The case 104 is tubular with a hollow 1501 for mounting the puncture needle cartridge 101 and the mounting member 102 and, at positions opposite to each other on a wall portion 1502 formed around the hollow 1501, has two helical slits 501 through the wall portion 1502. When the mounting member 102 is mounted in the case 104, the slit 501 holds the boss 503 of the mounting member 102 such that the boss 503 can slide along the slit 501. An edge 1504 being on the side opposite to the edge 1503 and exposed in the slit 501 of the wall portion 1502 limits the movement of the boss 503, and thereby prevents the puncture needle cartridge 101 from excessively pressing the mounting member 102 in the mounting direction of the mounting member 102. The case 104 is also provided with a projection 1505 projecting near the edge 1504 in the slit 501 (see FIG. 16C). When the protective cap 112 is separated from the lancet body 110, that is, when the insertion of the puncture needle cartridge 101 into the puncture instrument body 105 is completed, the projection 1505 is engaged with the boss 503 of the mounting member 102 to function as a stopper which limits the boss 503 such that it does not return in the direction of an arrow 1506.

An operation of mounting the puncture needle cartridge 101 in the puncture instrument body 105 in the puncture device 100 configured as above will be described with reference to FIGS. 1, 16, and 17. FIGS. 16 and 17 show an operation of mounting the puncture needle cartridge 101 in the puncture instrument body 105.

First, the lancet 204 is inserted into the puncture needle holder 113 to engage the lug portion 209 of the protective cap 112 with the flange portion 211 of the puncture needle holder 113 and to engage the cross-shaped rib 210 of the lancet body 110 with the long holes 702 of the puncture needle holder 113, and thus the puncture needle cartridge 101 is completed in which the lancet 204 and the puncture needle holder 113 are fixed in an integrated manner.

Figure 16A:
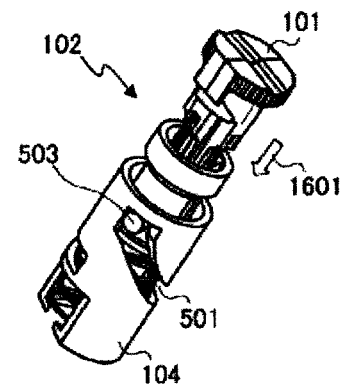
FIG. 16A shows a state where the insertion of the puncture needle cartridge for mounting the puncture needle cartridge in a puncture instrument body is started, according to Embodiment 1 of the invention.

Then, the mounting member 102 and return spring 103 attached in advance to the puncture instrument body 105 are pressed in the mounting direction of the mounting member 102 by the puncture needle cartridge 101. FIG. 16A shows a state where the insertion of the puncture needle cartridge 101 into the puncture instrument body 105 is started. At this time, the cuts 703 of the puncture needle holder 113 comprising the puncture needle cartridge 101 are engaged with the projections 601 of the mounting member 102, and this engagement limits the rotation of the lancet body 110 and puncture needle holder 113 about the shaft center of the lancet body 110, the rotation axis P, against the mounting member 102, and causes the puncture needle holder 113 to work with the movement of the mounting member 102.

Figure 17A:
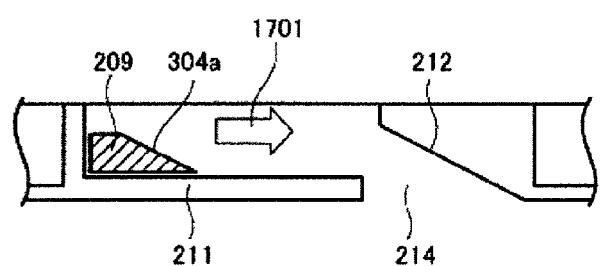
FIG. 17A shows a state where the insertion of the puncture needle cartridge for mounting the puncture needle cartridge in the puncture instrument body is started, according to Embodiment 1 of the invention.

FIG. 17A shows the state of FIG. 16A, that is, the state of an initial position where the puncture needle cartridge 101 is inserted in the mounting member 102. In the FIG. 17A, the movement of the lug portion 209 in the direction in which the protective cap 112 comes off (the downward direction in FIG. 17) is limited by the flange portion 211, and therefore the protective cap 112 does not come off even if a force acts in the direction to pull out the protective cap 112 (the direction opposite to the mounting direction of the mounting member 102 (the direction opposite to the direction of an arrow 1601 in FIG. 16A)).

Figure 16B:
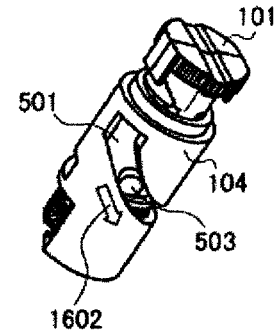
FIG. 16B shows a state where the insertion of the puncture needle cartridge for mounting the puncture needle cartridge in the puncture instrument body is on the way, according to Embodiment 1 of the invention.

Then, if the mounting member 102 is further pressed in the mounting direction of the mounting member 102 (the direction of the arrow 1601 in FIG. 16A) from the state of FIG. 16A to the state of FIG. 16B by the puncture needle cartridge 101, the boss 503 of the mounting member 102 is guided by the slit 501 of the case 104 to slide in the direction of an arrow 1602 in FIG. 16, and therefore the puncture needle cartridge 101 rotates about the shaft center of the lancet body 110, the rotation axis P. At this time, as shown in FIG. 17A, the lug portion 209 starts to move along the flange portion 211 toward the notch 214 (the rightward direction in FIG. 17). Since the mounting member 102 and the puncture needle holder 113 are engaged with each other, the rotation of the mounting member 102 causes the puncture needle holder 113 to rotate simultaneously. Then, since the cross-shaped rib 210 of the lancet body 110 and the cross-shaped groove 213 of the puncture needle holder 113 are engaged with each other, the side of the lancet body 110 rotates. On the other hand, since the protective cap 112 is grasped by a user's hand or the like for inserting the puncture needle cartridge 101, the rotation of the protective cap 112 about the shaft center of the lancet body 110, the rotation axis P, is prevented, and the connection 208 provided on the lancet body 110 is subjected to a force similar to a twisting and cutting off operation (see FIGS. 4 and 7).

Figure 17B:
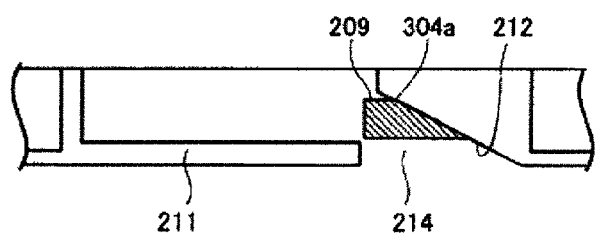
FIG. 17B shows a state where the insertion of the puncture needle cartridge for mounting the puncture needle cartridge in the puncture instrument body is on the way, according to Embodiment 1 of the invention.

When the mounting member 102 is further pressed in the mounting direction of the mounting member 102 (the direction of the arrow 1601 in FIG. 16A) by the puncture needle cartridge 101, the slope portion 304a of the lug portion 209 provided on the protective cap 112 comes in contact with the slope portion 212 as shown in FIG. 17B.

When the puncture needle cartridge 101 is rotated to the angle of FIG. 17B, the lug portion 209 reaches the position of the notch 214 where the flange portion 211 of the puncture needle holder 113 is cut out. At this point, the connection 208 of the lancet body 110 is cut off without fail. The angle of rotation of the mounting member 102 from the initial position for the connection 208 to be cut off without fail is preferably between 90 and 270 degrees, and more preferably between 120 and 180 degrees.

Figure 16C:
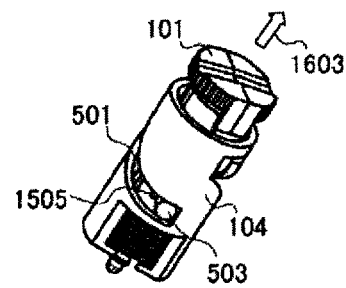
FIG. 16C shows a state where the insertion of the puncture needle cartridge for mounting the puncture needle cartridge in the puncture instrument body is completed, according to Embodiment 1 of the invention.

Then, when the puncture needle cartridge 101 is further rotated in the direction of the arrow 220 (see FIG. 2), the boss 503 of the mounting member 102 as shown in FIG. 16c reaches the edge 1504 exposed in the slit 501 of the case 104 (see FIG. 14), preventing the puncture needle cartridge 101 from rotating any more. The state of FIG. 16C is the state of insertion completion. In the state of FIG. 16C, the boss 503 is engaged with the projection 1505 to limit the movement of the puncture needle cartridge 101 in the ejection direction (the direction of an arrow 1603).

Figure 17C:
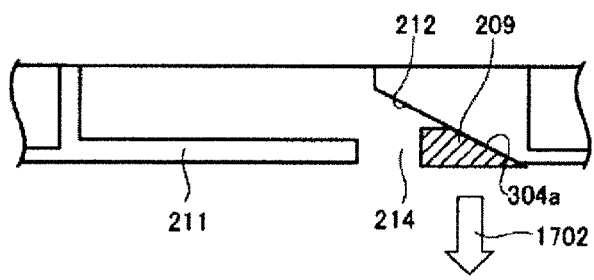
FIG. 17C shows a state where the insertion of the puncture needle cartridge for mounting the puncture needle cartridge in the puncture instrument body is completed, according to Embodiment 1 of the invention.

When the state of FIG. 16C is reached, the lug portion 209 of the protective cap 112 slides along the slope portion 212 of the puncture needle holder 113 and therefore, as shown in FIG. 17C, the protective cap 112 slides in the direction of an arrow 1702 in which it comes off from the puncture needle holder 113 to be able to be separated from the lancet body 110.

An operation of disposing of the puncture needle cartridge 101 will next be described with reference to FIG. 18.

Figure 18A:
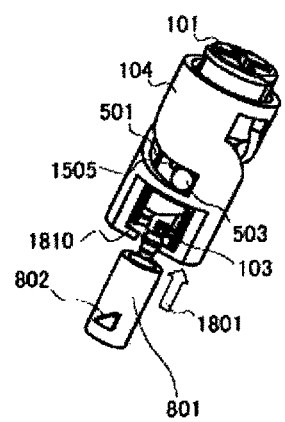
FIG. 18A shows a start state (initial state) of an operation of ejecting the puncture needle cartridge according to Embodiment 1 of the invention.

FIG. 18A shows a start state (initial state) of an operation of ejecting the puncture needle cartridge 101. In the initial state, since the return spring 103 is in contact with an inside bottom surface 1810 of the case 104 at the lower end and is pressed in the mounting direction of the mounting member 102 by the mounting member 102, the return spring 103 is elastically deformed and biases upward (in the direction of an arrow 1801) the mounting member 102 in which the puncture needle cartridge 101 is inserted.

At this point, the puncture needle cartridge 101 is mounted in the mounting member 102; the boss 503, which is the guiding portion provided on the mounting member 102, and the slit 501, which is the guided portion provided on the case 104, are engaged with each other; and the puncture needle cartridge 101 is held on the rear-end side of the slit 501. This is done in such a way that when the puncture needle cartridge 101 is inserted into the puncture instrument body 105, the boss 503 of the mounting member 102 goes over the projection 1505 formed in the rear end and upper side of the slit 501 on the case 104 and is thus locked by the projection 1505. Additionally, since the return spring 103 is in contact with the inside bottom surface 1810 of the case 104 at the lower end and is pressed in the mounting direction of the mounting member 102 by the mounting member 102, the return spring 103 is elastically deformed. As a result, the return spring 103 biases in the direction of the arrow 1801 the mounting member 102 in which the puncture needle cartridge 101 is inserted, and therefore the force causing the boss 503 to return in the direction of an arrow 1802 locks the boss 503 and the projection 1505 to each other once the boss 503 goes over the projection 1505.

The ejection rod 801 (ejection member) incorporated in the puncture instrument body 105 is provided with the triangular lug 802, and the ejection operation is started by the ejection rod 801 moving toward the front end of the puncture instrument body 105 (the ejection direction of the puncture needle cartridge 101 (the direction of the arrow 1801)). An operation of a not-shown operation button provided on the outside of the puncture instrument body 105 allows the ejection rod 801 to move in the direction of the arrow 1801 integrally with or in conjunction with the operation button.

Figure 18B:
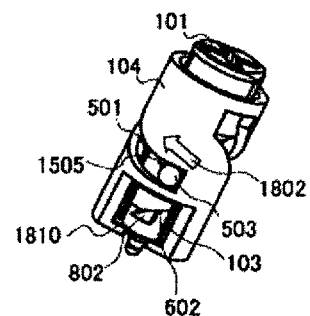
FIG. 18B shows a state where a lock between a projection of the case and a boss of the mounting member is released, according to Embodiment 1 of the invention.

FIG. 18B shows a state where the lock between the projection 1505 of the case 104 and the boss 503 of the mounting member 102 is released by the triangular lug 802 of the ejection rod 801. Contact between the triangular lug 802 of the ejection rod 801 and the slope portion 602 of the mounting member 102 changes the force in the direction of the arrow 1801 in FIG. 18 into a force in a direction perpendicular to the direction of the arrow 1801, causing the boss 503 to go over the projection 1505 to release the engagement between the boss 503 and the projection 1505, and the lock is released. Then, the boss 503 is guided by the slit 501 to slide in the direction of the arrow 1802, and the mounting member 102 starts to rotate about the rotation axis P.

Figure 18C:
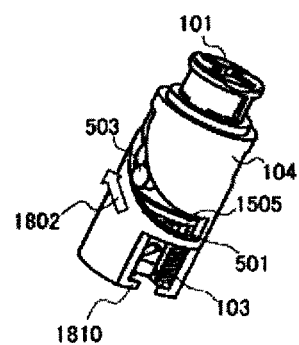
FIG. 18C shows a motion after the release of the lock between the boss and the projection according to Embodiment 1 of the invention.

FIG. 18C shows a motion after the release of the lock between the boss 503 and the projection 1505. When the lock between the projection 1505 and the boss 503 of the mounting member 102 is released, the restoring force of the return spring 103 biasing the mounting member 102 in the direction opposite to the mounting direction of the mounting member 102 (the upward direction in FIG. 1) causes the mounting member 102 to move toward the front end of the puncture instrument body 105, and the engagement of the puncture needle cartridge 101 with the plunger 901 of the puncture instrument is also released.

Figure 18D:
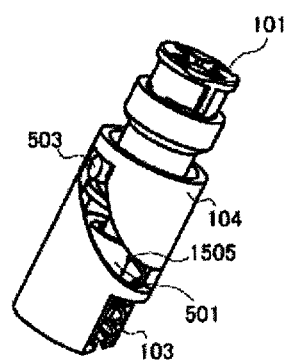
FIG. 18D shows a completion state of the operation of ejecting the puncture needle cartridge according to Embodiment 1 of the invention.

FIG. 18D shows a completion state of the operation of ejecting the puncture needle cartridge 101.

As just described, the embodiment allows the operation of twisting and cutting off the protective cap to be carried out in parallel with the operation of inserting the puncture needle cartridge, and can therefore reduce the burden on patients during operation. The embodiment can also facilitate the ejection operation of the puncture needle cartridge through the return spring biasing the mounting member in the direction of ejecting the mounting member when the mounting member is mounted in the puncture instrument body. In the embodiment, the flange portion formed on the puncture needle holder for preventing the protective cap from coming off eliminates: a release of the normal grasp of the lancet body by the puncture instrument (the plunger); a change in the depth of puncture; or protrusion of the tip of the puncture needle of the lancet from the puncture instrument, and needle stick accidents caused by the protruding puncture needle can be prevented. In the embodiment, the slit of the case limiting the movement of the boss formed on the mounting member can prevent both from excessively rotating clockwise or counterclockwise about the rotation axis P, so that a breakage of the puncture needle cartridge or the like can be prevented and needle stick accidents can be prevented.

Embodiment 2

Figure 19:
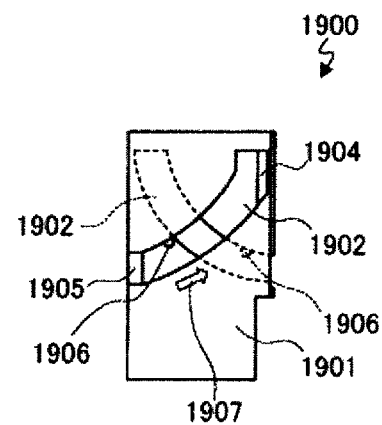
FIG. 19 is a front view of a case according to Embodiment 2 of the invention.

FIG. 19 is a front view of a case 1900 according to Embodiment 2 of the invention. The configuration of the embodiment is the same as that of the above-described Embodiment 1 except the case 1900, and therefore will not be described. In the description of the case 1900 of the embodiment, like symbols to those of Embodiment 1 will be used for like components to those of Embodiment 1 except the case 104.

The embodiment is characterized in that, instead of the slit 501 of the case 104 of the above-described Embodiment 1, a reverse helical slit 1902 opposed to the helical slit 501 is formed on the case 1900.

The case 1900 is tubular with a hollow for mounting the puncture needle cartridge 101 and the mounting member 102 and, on a wall portion 1901 forming the hollow, has helical slits 1902 through the wall portion 1901. When the mounting member 102 is mounted in the case 1900, the slit 1902 holds the boss 503 of the mounting member 102 such that the boss 503 can slide along the slit 1902. An edge 1905, on the opposite side of the edge 1904, exposed in the slit 1902 of the wall portion 1901 limits the movement of the boss 503, and thereby prevents the puncture needle cartridge 101 from excessively pressing the mounting member 102 in the mounting direction of the mounting member 102. The case 1900 is also provided with a projection 1906 projecting near the edge 1905 in the slit 1902 (see FIG. 19). When the protective cap 112 is separated from the lancet body 110, that is, when the insertion of the puncture needle cartridge 101 into the puncture instrument body 105 is completed, the projection 1906 is engaged with the boss 503 of the mounting member 102 to function as a stopper which limits the boss 503 such that it does not return in the direction of an arrow 1907. The rest of the configuration of the case is the same as that of the above-described Embodiment 1, and therefore will not be described.

Figure 20:
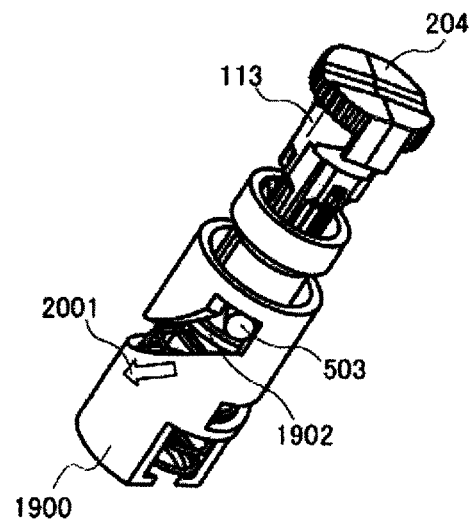
FIG. 20 shows an operation of inserting a puncture needle cartridge into a mounting member and the case according to Embodiment 2 of the invention.

FIG. 20 shows a state where the mounting member 102 is pressed by the puncture needle cartridge 101 in the direction of mounting the mounting member 102 in the puncture instrument body 105.

In FIG. 20, when the mounting member 102 is pressed by the puncture needle cartridge 101 in the direction of mounting the mounting member 102 in the puncture instrument body 105, the boss 503 of the mounting member 102, being guided by and engaged with the slit 1902, slides in the direction of an arrow 2001. On the other hand, when the puncture needle cartridge 101 is ejected, the boss 503 slides within the slit 1902 in the direction opposite to the direction of the arrow 2001, causing the puncture needle cartridge 101 to be ejected from the puncture instrument body 105. In FIG. 20, the projection 1906 is not illustrated for convenience of description.

As just described, the embodiment allows the operation of twisting and cutting off the protective cap to be carried out in parallel with the operation of inserting the puncture needle cartridge into the puncture instrument body, and can therefore reduce the burden on patients during operation. The embodiment can also facilitate the ejection operation of the puncture needle cartridge through the return spring biasing the mounting member in the direction of ejecting the mounting member when the mounting member is mounted in the puncture instrument body. In the embodiment, the flange portion formed on the puncture needle holder for preventing the protective cap from coming off eliminates: a release of the normal grasp of the lancet body by the puncture instrument (the plunger); a change in the depth of puncture; or protrusion of the tip of the puncture needle of the lancet from the puncture instrument, and needle stick accidents caused by the protruding puncture needle can be prevented. In the embodiment, the slit of the case limiting the movement of the boss formed on the mounting member can prevent both from excessively rotating clockwise or counterclockwise about the rotation axis P, so that a breakage of the puncture needle cartridge or the like can be prevented and needle stick accidents can be prevented.

Embodiment 3

Figure 21A:
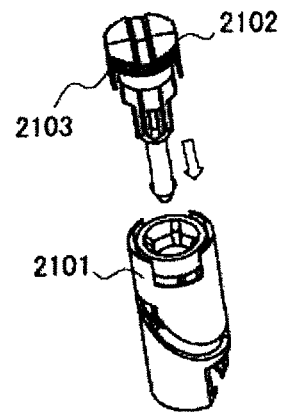
FIG. 21A shows a state where the insertion of a puncture needle cartridge for mounting the puncture needle cartridge in a mounting member and case is started, according to Embodiment 3 of the invention.
Figure 21B:
FIG. 21B shows a state where the insertion of the puncture needle cartridge for mounting the puncture needle cartridge in the mounting member and case is on the way, according to Embodiment 3 of the invention.
Figure 21C:
FIG. 21C shows a state where the insertion of the puncture needle cartridge for mounting the puncture needle cartridge in the mounting member and case is completed, according to Embodiment 3 of the invention.
Figure 22:
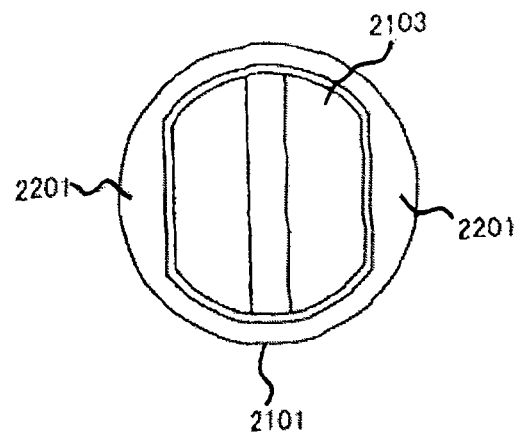
FIG. 22 is a top view of the puncture needle cartridge mounted in the case according to Embodiment 3 of the invention.

FIG. 21 shows an operation of mounting the puncture needle cartridge in the case according to Embodiment 3 of the invention, and FIG. 22 is a top view of the puncture needle cartridge mounted in the case viewed from the top. FIG. 21A shows a state where the insertion of the puncture needle cartridge for mounting the puncture needle cartridge in the mounting member and case is started, according to Embodiment 3 of the invention; FIG. 21B shows a state where the insertion of the puncture needle cartridge for mounting the puncture needle cartridge in the mounting member and case is on the way, according to Embodiment 3 of the invention; and FIG. 21C shows a state where the insertion of the puncture needle cartridge for mounting the puncture needle cartridge in the mounting member and case is completed, according to Embodiment 3 of the invention. The configuration of the embodiment except a protective cap 2102 and case 2101 is the same as that of the above-described Embodiment 1, and therefore will not be described.

The embodiment is characterized in that the shape of the protective cap 2102 and the shape of a front end of the case 2101 are complementary to each other and given a directional property.

As shown in FIG. 21A, the protective cap 2102 has a flange portion 2103 having a shape of a circle cut out partly.

The front end of the case 2101 is formed into a complementary shape, corresponding to the shape of the flange portion 2103 of the protective cap 2102, which can be engaged therewith in a male-female manner. That is, the case 2101 has a thick-walled portion 2201 (limit portion, see FIG. 22) which corresponds to the portion of the cut-out shape of the flange portion 2103 and is made thick.

The rest of the configurations of the protective cap 2102 and case 2101 are the same as those of the protective cap 112 and case 104 of Embodiment 1, and therefore will not be described.

In the embodiment, when the puncture needle cartridge is inserted into the mounting member 102 mounted in the case 2101, the flange portion 2103 is engaged with the case 2101 to limit the rotation about the rotation axis P.

As described above, in addition to the advantages of the above-described Embodiment 1, the embodiment employs the shape of the flange portion of the protective cap and the shape of the front portion of the case which are complementary to each other and can be engaged with each other in a male-female manner, thereby being able to limit the rotation of the protective cap about the shaft center of the lancet body, the rotation axis P, and can therefore eliminate a mistake in twisting and cutting off the protective cap due to an operation mistake of a patient. Since in the embodiment the protective cap does not require to be grasped by a hand or the like, ease of operation of the twisting and cutting off can be improved.

While in the embodiment the circular shape of the flange portion of the protective cap is partly cut out to make the shape of the protective cap and the shape of the front end of the case be complementary to each other, the invention is not limited to this and another method may be employed to make the shape of the protective cap and the shape of the front end of the case be complementary to each other. The protective cap and the case do not necessarily require to be complementary to each other, and the case 2101 may be provided with a limit member which is engaged with the flange portion 2103 of the protective cap to limit the direction of rotation so that the protective cap does not rotate together with the puncture needle holder 113 and the mounting member 102. The complementary shape, however, has no backlash and play, and can therefore reliably limit the rotation of the protective cap.

Embodiment 4

Figure 23:
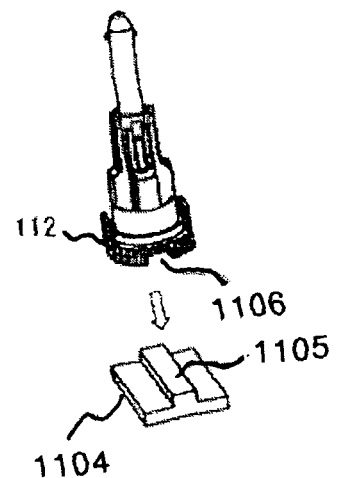
FIG. 23 is a perspective view of a puncture needle cartridge and fixing base according to Embodiment 4 of the invention.
Figure 24:
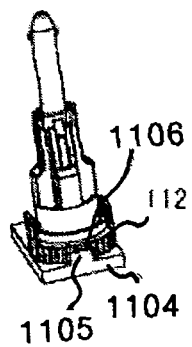
FIG. 24 is a perspective view of the puncture needle cartridge and fixing base according to Embodiment 4 of the invention.
Figure 25:
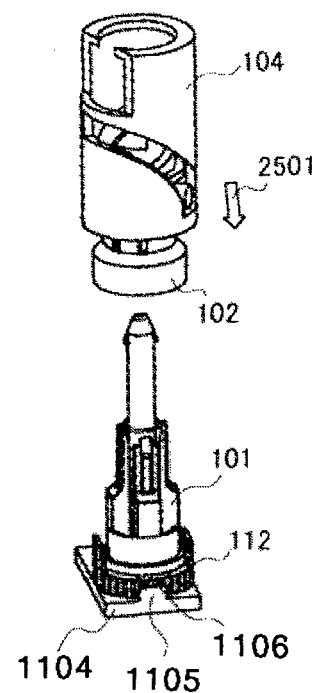
FIG. 25 shows an operation of inserting the puncture needle cartridge into a mounting member and case according to Embodiment 4 of the invention.

FIGS. 23, 24, and 25 show an operation of mounting the puncture needle cartridge in the case according to Embodiment 4 of the invention. In the embodiment, the configuration of the puncture device is the same as that of the above-described Embodiment 1, and therefore will not be described.

The embodiment is characterized in that a fixing member 1104 is provided to prevent the rotation of the protective cap 112 about the shaft center of the lancet body 110, the rotation axis P, and that the protective cap 112 is provided with a groove or the like which corresponds to the shape of the fixing member 1104.

The fixing member 1104 has a projection 1105 to be engaged with a groove 1106 of the protective cap 112.

In the embodiment, with the projection 1105 of the fixing member 1104 and the groove 1106 of the protective cap 112 being engaged with each other as shown in FIG. 24, the puncture device 100 having the mounting member 102 (only the mounting member 102 and the case 104 are illustrated in FIG. 25) is pressed in the direction of an arrow 2501 against the puncture needle cartridge 101 as shown in FIG. 25. During this time, the protective cap 112 is limited by the fixing member 1104 so as not to rotate about the rotation axis P.

As described above, in addition to the advantages of the above-described Embodiment 1, the embodiment uses the fixing member to limit the rotation of the protective cap about the shaft center of the lancet body, thereby eliminating the need to grasp the protective cap with a hand, and can eliminate a mistake in twisting and cutting off the protective cap due to an operation mistake of a patient. Since in the embodiment the operation of twisting and cutting off the protective cap can be done by one hand, ease of operation of the twisting and cutting off can be improved.

Embodiment 5

Figure 26:
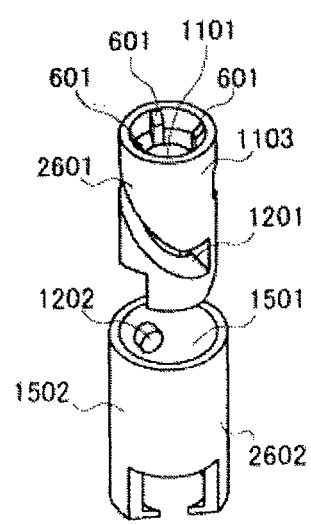
FIG. 26 is a perspective view of a case and mounting member according to Embodiment 5 of the invention.

FIG. 26 is a perspective view of a case and a mounting member according to Embodiment 5 of the invention. In the embodiment, the configuration except the case and mounting member is the same as that of the above-described Embodiment 1, and therefore will not be described.

The embodiment is characterized in that, instead of the boss 503 provided on the mounting member 102 and the slit 501 formed on the case of the above-described Embodiment 1, a slit 1201 is formed on a mounting member 2601 and a boss 1202 is formed on a case 2602.

The mounting member 2601 is tubular with a hollow 1101 into which the puncture needle cartridge 101 is inserted, and has the helical slit 1201 on a wall portion 1103 formed around the hollow 1101.

The case 2602 has a hollow 1501 for receiving the mounting member 2601, and has the boss 1202 which protrudes in the hollow 1501 from a wall portion 1502 formed around the hollow 1501. The boss 1202 is engaged with the slit 1201, and is guided by the slit 1201 to slide with the engagement with the slit 1201 being kept when the mounting member 2601 is pressed in the mounting direction of the mounting member 2601 by the puncture needle cartridge 101. While this allows the mounting member 2601 and the puncture needle holder 113 and lancet body 110 comprising the puncture needle cartridge 101 to rotate about the shaft center of the lancet body 110, the rotation axis P, the protective cap 112 is prevented from rotating about the shaft center of the lancet body 110, the rotation axis P, and therefore the protective cap 112 and the lancet body 110 are separated from each other at the connection 208 provided on the lancet body 110.

The rest of the configurations of the mounting member 2601 and case 2602 are the same as those of the mounting member 102 and case 104 of the above-described Embodiment 1, and therefore will not be described.

As just described, the embodiment allows the operation of twisting and cutting off the protective cap to be carried out in parallel with the operation of inserting the puncture needle cartridge into the puncture instrument body, and can therefore reduce the burden on patients during operation. The embodiment can also facilitate the ejection operation of the puncture needle cartridge through the return spring biasing the mounting member in the direction of ejecting the mounting member when the mounting member is mounted in the puncture instrument body. In the embodiment, the flange portion formed on the puncture needle holder for preventing the protective cap from coming off eliminates: a release of the normal grasp of the lancet body by the puncture instrument (the plunger); a change in the depth of puncture; or protrusion of the tip of the puncture needle of the lancet from the puncture instrument, and needle stick accidents caused by the protruding puncture needle can be prevented. In the embodiment, the slit of the case limiting the movement of the boss formed on the mounting member can prevent both from excessively rotating clockwise or counterclockwise about the rotation axis P, so that a breakage of the puncture needle cartridge or the like can be prevented and needle stick accidents can be prevented.

In the above-described embodiments an example has been described in which the boss or slit formed on the mounting member and the slit or boss formed on the case are engaged with each other to rotate the mounting member, the puncture needle holder, and the lancet body about the shaft center of the lancet body. However, the invention is not limited to this, and any configuration can be adopted as long as it is a mechanism capable of guiding the rotation about the shaft center of the lancet body. While in the above-described embodiments an example has been described in which the case and the puncture instrument body are separated from each other, the invention is not limited to this, and the puncture instrument body may also be used as the case with the slit or boss being formed on the puncture instrument body.

The disclosure of the specification, drawings, and abstract included in Japanese Patent Application No. 2008-058436 filed on Mar. 7, 2008 is entirely incorporated herein.

INDUSTRIAL APPLICABILITY

The puncture device according to the invention is suited for blood sampling in blood measurements including, in particular, blood sugar measurements.

The invention claimed is:

1. A puncture device comprising:
 a puncture needle cartridge including:
  a rod-like lancet body having a puncture needle at one end and a grip part to be held by a puncture device body at an opposing end;
  a protective cap for covering and protecting the puncture needle and formed integrally with the rod-like lancet body; and
  a puncture needle holder engaged with the rod-like lancet body to rotate together with the rod-like lancet body about a shaft center axis of rotation of the rod-like lancet body;
 a mounting member for holding the puncture needle cartridge such that the puncture needle cartridge can be inserted and removed therefrom; and
 a case mounted with the mounting member and held by the puncture device body,
 wherein the case includes a guiding portion for guiding a rotation of the mounting member about the axis of rotation,
 wherein the mounting member includes an external guided portion engaged with the guiding portion of the case,
 wherein the mounting member is engaged with the puncture needle holder and rotates together with the puncture needle holder about the axis of rotation by having the guided portion guided by the guiding portion as a result of being pressed by the puncture needle cartridge in a direction of mounting in the case,
 wherein the protective cap is prevented from rotating about the axis of rotation during the pressing of the puncture needle cartridge and is separated from the rod-like lancet body by the rotation of the mounting member about the axis of rotation,
 wherein the puncture needle holder includes cuts,
 wherein the mounting member includes internal projections, and
 wherein the cuts of the puncture needle holder are engaged by the internal projections of the mounting member, such that the puncture needle holder is held by the engagement of the cuts and the internal projections so as to limit a rotation of the puncture needle holder against the mounting member and about the axis of rotation.

2. The puncture device according to claim 1,
 wherein the case is tubular with a first hollow for mounting the mounting member,
 wherein the guiding portion of the case, is helical, and is located on a first wall portion formed around the first hollow,
 wherein the mounting member is tubular with a second hollow for insertion of the puncture needle cartridge, and
 wherein the guided portion of the mounting member, is slidably engaged with the guiding portion, and is located a second wall portion formed around the second hollow.

3. The puncture device according to claim 1,
 wherein the case includes a slit as the guiding portion, and
 wherein the mounting member includes a protrusion as the guided portion.

4. The puncture device according to claim 1,
 wherein the protective cap includes a limit portion which is engaged with the case, and
 wherein the rotation of the protective cap about the axis of rotation is limited when the puncture needle cartridge is inserted into the mounting member mounted on the case.

5. The puncture device according to claim 1, wherein the mounting member rotates clockwise or counterclockwise about the axis of rotation through the guided portion guided by the guiding portion.

6. The puncture device according to claim 1, further including:
 an ejection member which is in contact with the mounting member to press the mounting member in an ejection direction of the puncture needle cartridge opposite to the mounting direction; and
 an elastic member placed between the case and the mounting member for biasing the mounting member in the ejection direction when the mounting member is pressed in the mounting direction,
 wherein, when the protective cap is separated from the lancet body, the mounting member is engaged with the case and a movement of the mounting member in the ejection direction is limited, and when the mounting member is pressed in the ejection direction by the ejection member, the engagement of the mounting member with the case is released and the mounting member moves in the ejection direction through the biasing force of the elastic member to allow the puncture needle cartridge to be ejected.

7. The puncture device according to claim 1, further including a fixing member engaged with the protective cap to thereby prevent the protective cap from rotating about the axis of rotation when the mounting member is pressed in the mounting direction by the puncture needle cartridge.

8. A puncture device comprising:
 a puncture needle cartridge including:
  a rod-like lancet body having a puncture needle at one end and a grip part to be held by a puncture device body at an opposing end;
  a protective cap for covering and protecting the puncture needle and formed integrally with the rod-like lancet body; and
  a puncture needle holder engaged with the rod-like lancet body to rotate together with the rod-like lancet body about a shaft center axis of rotation of the rod-like lancet body;

a mounting member for holding the puncture needle cartridge such that the puncture needle cartridge can be inserted and removed therefrom; and a case mounted with the mounting member and held by the puncture device body, wherein the mounting member is engaged with the puncture needle holder and rotates together with the puncture needle holder about the axis of rotation by having a guiding portion guiding a guided portion formed on the case when pressed by the puncture needle cartridge in a direction of mounting in the case, wherein the protective cap is prevented from rotating about the axis of rotation during the pressing of the puncture needle cartridge and is separated from the rod-like lancet body by the rotation of the mounting member about the axis of rotation, wherein the puncture needle holder includes cuts, wherein the mounting member includes internal projections, and wherein the cuts of the puncture needle holder are engaged by the internal projections of the mounting member, such that the puncture needle holder is held by the engagement of the cuts and the internal projections so as to limit a rotation of the puncture needle holder against the mounting member and about the axis of rotation.

9. The puncture device according to claim 8, wherein the mounting member is tubular with a first hollow for insertion of the puncture needle cartridge, wherein the guiding portion of the mounting member is helical and is located on a first wall portion formed around the first hollow, wherein the case is tubular with a second hollow for mounting the mounting member, and wherein the guided portion of the case is slidably engaged with the guiding portion and is located on a second wall portion formed around the second hollow.

10. The puncture device according to claim 8, wherein the mounting member includes a slit as the guiding portion, and wherein the case includes a protrusion as the guided portion.

11. A puncture device comprising:

a puncture needle cartridge including:
  a rod-like lancet body having a puncture needle at one end and a grip part to be held by a puncture device body at an opposing end;
  a protective cap for covering and protecting the puncture needle and formed integrally with the rod-like lancet body; and
  a puncture needle holder engaged with the rod-like lancet body;

a mounting member for holding the puncture needle cartridge such that the puncture needle cartridge can be inserted and removed therefrom; and a case mounted with the mounting member and comprising the puncture device body, wherein the case cooperates with the mounting member and rotates, about an axis of rotation, the puncture needle holder engaged with the mounting member when the mounting member is pressed by the puncture needle cartridge in a direction of mounting in the case, wherein the protective cap is prevented from rotating abut the axis of rotation during the pressing of the puncture needle cartridge and is separated from the rod-like lancet body by the rotation of the mounting member about the axis of rotation, wherein the puncture needle holder includes cuts, wherein the mounting member includes internal projections, and wherein the cuts of the puncture needle holder are engaged by the internal projections of the mounting member, such that the puncture needle holder is held by the engagement of the cuts and the internal projections so as to limit a rotation of the puncture needle holder against the mounting member and about the axis of rotation.

\* \* \* \* \*